US00PP36712P3

(12) United States Plant Patent
Olesen

(10) Patent No.: US PP36,712 P3
(45) Date of Patent: Jun. 3, 2025

(54) MINIATURE ROSE PLANT NAMED 'Poulpah107'

(50) Latin Name: *Rosa hybrida*
Varietal Denomination: Poulpah107

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 0 days.

(21) Appl. No.: 18/831,193

(22) Filed: Sep. 5, 2024

(65) Prior Publication Data

US 2025/0107464 P1 Mar. 27, 2025

(30) Foreign Application Priority Data

Sep. 22, 2023 (QZ) ..... PBR 20231975

(51) Int. Cl.
*A01H 5/02* (2018.01)
*A01H 6/74* (2018.01)

(52) U.S. Cl.
USPC ..... Plt./118

(58) Field of Classification Search
USPC ..... Plt./101, 116, 118
See application file for complete search history.

*Primary Examiner* — Susan McCormick Ewoldt

(57) ABSTRACT

A new garden rose plant of the Miniature class which has abundant, yellow flowers and attractive foliage. This new and distinct variety has shown to be uniform and stable in the resulting generations from asexual propagation.

1 Drawing Sheet

Botanical designation: *Rosa hybrida.*

Variety denomination: 'Poulpah107'.

This application claims priority to Plant Breeder's Rights Application Number 2023/1975, which was filed at the Community Plant Variety Rights Office in the European Union on Sep. 22, 2023, the contents of which are hereby incorporated by reference for all purposes.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2015 and the resulting seeds were planted in a controlled environment in Fredensborg, Denmark. The new variety, named 'Poulpah107', originated as a single seedling from the stated cross.

The new variety may be distinguished from its male pollen parent and female seed parent primarily by the following characteristics. The male pollen parent plant has yellow flowers and grows to 30 cm height in one season while the claimed plant has similar color flowers yet grows to 42 cm in height. The female seed parent plant has yellow orange flowers while the new variety has yellow flowers.

The objective of the hybridization of this rose variety was to create a new and distinct variety with unique qualities, such as:

1. Uniform and abundant yellow flowers;
2. Vigorous, but compact growth when propagated on its own roots;
3. Exceptional disease resistance.

This combination of qualities is not present in previously available commercial cultivars of this type, known to the inventor, and distinguish 'Poulpah107' from all other varieties of which we are aware.

As part of the rose development program, Mogens N. Olesen germinated the seeds from the aforementioned hybridization during winter of 2015 and conducted evaluations on the resulting seedlings in a controlled environment in Fredensborg, Denmark. 'Poulpah107' was selected in the spring of 2016 by the inventor as a single plant from the progeny of the aforementioned hybridization.

Asexual reproduction of 'Poulpah107' by rooted cuttings was first done by Mogens N. Olesen in the nursery in Fredensborg, Denmark in July 2016. This initial and other subsequent asexual propagations conducted in controlled. environments have demonstrated that the characteristics of 'Poulpah107' are true to type and are transmitted from one generation to the next.

DESCRIPTION OF THE DRAWING

The accompanying color illustration shows as true as is reasonably possible to obtain in color photographs of this type, the typical characteristics of the buds, flowers, leaves, and stems, of 'Poulpah 107'. Specifically illustrated in the drawing are open flowers viewed from above and the side, a partially open flower on the stem, flower petals detached revealing reproductive flower parts and receptacle, mature leaves viewed from above and underneath, bare stems. Plants shown in the drawing are 6 months old.

DETAILED DESCRIPTION OF THE VARIETY

The following is a description of 'Poulpah107', as observed in its growth in a glasshouse located in Odense Denmark. Observed plants are 6 months of age, and were grown on their own roots in 24 cm containers. Color references are made using The Royal Horticultural Society (London, England) Colour Chart, 2001, except where common terms of color are used.

For a comparison, several physical characteristics of the rose variety 'Poulpah095', U.S. Plant Pat. No. 32,780 are now compared to 'Poulpah107'. General tonality of flower color of the comparison variety is Yellow Group 12A, while the claimed plant is Yellow Group 13A. 'Poulpah107' has 70 petals, while 'Poulpah095' has about 36 petals.

FLOWER AND FLOWER BUD

Blooming habit: Continuous.

Flower bud:

- *Size.*—Upon opening, 30 mm in length from base of receptacle to end of bud. Bud diameter. is 15 mm.
- *Bud form.*—Ovoid.
- *Sepal inner surface.*—Color: Yellow-Green Group 145B. Surface: Strongly pubescent.
- *Sepal outer surface.*—Color: Yellow-Green Group 144B. Texture: Smooth.
- *Sepal shape.*—Apex: Cirrhose. Base: Flat at union with receptacle.
- *Sepal margin.*—Margins have moderate foliaceous appendages on three of the five sepals.
- *Sepal size.*—25 mm long, 10 mm wide.
- *Receptacle.*—Texture: Smooth. Size: 5 mm in height, 7 mm wide. Color: Yellow-Green Group 144A. Shape: Funnel.
- *Pedicel.*—Surface: Smooth. Length: 40 mm. Diameter: 2.5 mm on average. Color: Yellow-Green Group 144A. Strength: Strong.

Flower bud development: Flower buds are borne single.

Flower bloom:

- *Fragrance.*—Light to moderate floral scent.
- *Duration.*—The blooms have a duration on the plant of approximately 21 days. Petals fall cleanly away from plant after flowers have fully matured.
- *Size.*—Flower diameter is 80 mm when open. Flower depth is 30 mm.
- *Flower shape.*—Star shaped, initially with a high center which is tightly closed. As flower mature they resemble a rounded pompon.
- *Shape of flower, side view.*—The upper portion is convex. The lower portion is deeply concave.

Petalage: Under normal conditions, flowers have about 70 petals.

General tonality of flower: Open flowers are Yellow Group 13A.

Petal color:

- *Upon opening, outer petals.*—Upper surface: Yellow Group 12A. Lower surface: Yellow Group 12B.
- *Upon opening, inner petals.*—Upper surface: Yellow-Orange Group 14A. Lower surface: Yellow-Orange Group 14B.
- *Basal petal spots, upon opening.*—No distinctive coloration at the petal base observed.
- *After opening, outer petals.*—Upper surface: Yellow Group 12B. Lower surface: Yellow Group 11A.
- *After opening, inner petals.*—Upper surface: Yellow Group 12B. Lower surface: Yellow Group 11A.

Petals:

- *Petal reflex.*—Strong bilateral.
- *Margin.*—Entire and uniform with no undulation.
- *Shape.*—Broad and elliptic. Apex shape: Rounded. Base shape: Acute.
- *Size.*—40 mm (l) 38 mm (w).
- *Texture.*—Smooth.
- *Thickness.*—Average.

Petaloids:

- *Size.*—15 mm (l) by 7 mm (w).
- *Quantity.*—About 10.
- *Shape.*—Elliptical with an acute base and rounded apices.
- *Color.*—Upper surface is Yellow-Orange Group 14A. Lower surface Yellow-Orange Group 14B.

Reproductive flower parts:

- *Pollen.*—None observed.
- *Anthers.*—Size: 2 mm in length. Color: Yellow Group 11C. Quantity: 45 on average.
- *Filaments.*—Color: Yellow Group 13D. Length: 6 mm.
- *Pistils.*—Length: 8 mm. Quantity: 28 on average.
- *Stigmas.*—Color: Greyed-Yellow Group 160D.
- *Styles.*—Color: Yellow-Green Group 145D.
- *Location of stigmas.*—Level in location relative to the length of the filaments and the height of the anthers.
- *Hips.*—None Observed.

PLANT

Plant growth: Upright. Plants are about 42 cm in height, and 35 cm wide.

Stems:

- *Color of juvenile growth.*—Yellow-Green Group 144B.
- *Color of mature growth.*—Yellow-Green Group 144A.
- *Length.*—Canes are about 34 cm from the base of the plant to the flowering portion.
- *Diameter.*—About 3 to 4 mm.
- *Internodes.*—About 40 mm between nodes.
- *Surface texture.*—Young wood: Smooth. Older wood: Smooth.

Long prickles: None observed.

Plant foliage:

- *Compound leaf.*—About 112 mm (l)×70 (w).
- *Quantity.*—2 leaves per 10 cm of stem on average.
- *Leaf bearing angle to the stem.*—45 degrees.
- *Color of juvenile foliage.*—Upper side: Yellow-Green Group 144A. Lower side: Yellow-Green Group 144B.
- *Color of mature foliage.*—Upper side: Yellow-Green Group 147A. Lower side: Yellow-Green Group 147B.

Plant leaves and leaflets:

- *Stipules.*—Size: 11 mm long, 2 to 3 mm wide. Quantity: 2 per compound leaf. Shape: Linear, slightly broad based with outward extending apices. Margins: Finely serrated. Color: Yellow-Green Group 144A.
- *Petiole.*—Length: 15 mm. Diameter: 2 mm. Upper surface color: Yellow-Green Group 144A. Lower surface color: Yellow-Green Group 144A.
- *Rachis.*—Length: 30 mm. Upper surface color: Yellow-Green Group 144A. Lower surface color: Yellow-Green Group 144A.
- *Leaflet.*—Quantity: Normally 5 to 7 leaflets. Margins: Serrated. Size: Terminal leaflets are about 45 mm long, 33 mm wide. Shape: Generally elliptical. Base: Rounded. Apex: Acute. Texture: Smooth. Thickness:

Average. Arrangement: Odd pinnate. Venation: Reticulate. Glossiness: Not glossy.

Disease resistance: Above average resistance to powdery mildew *Sphaerotheca pannosa* var. *rosae*, downy mildew *Peronospora sparsa*, rust *Phragmidium* spp., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant named 'Poulpah107' substantially as described and illustrated herein.

* * * * *

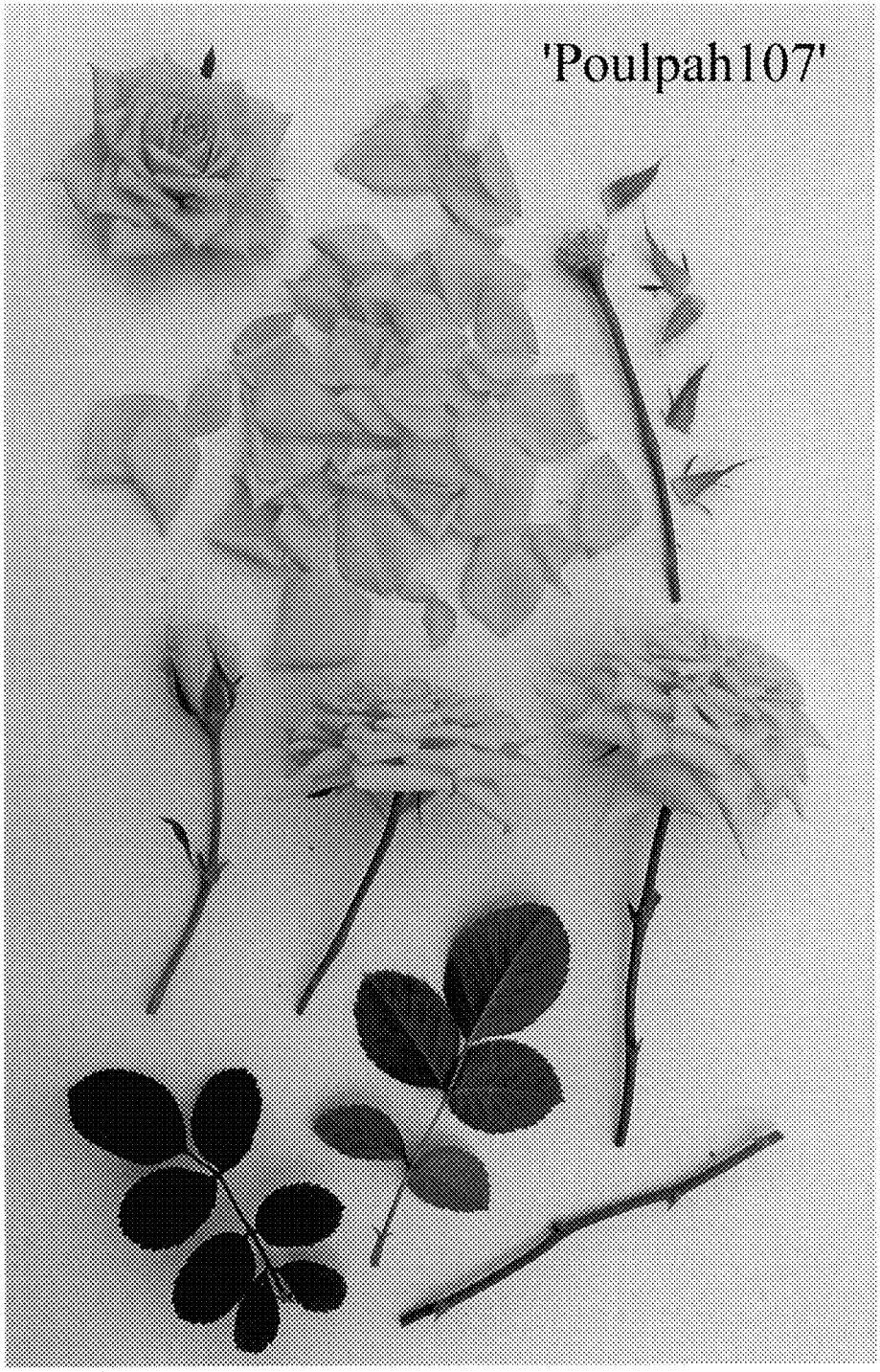
'Poulpah107'